United States Patent
Schubert et al.

(10) Patent No.: US 7,371,917 B2
(45) Date of Patent: May 13, 2008

(54) PREPARATION OF OLEFINS BY METATHESIS OVER A CARBIDE OR OXYCARBIDE OF A TRANSITION METAL

(75) Inventors: Markus Schubert, Ludwigshafen (DE); Till Gerlach, Ludwigshafen (DE); Michael Hesse, Worms (DE); Juergen Stephan, Mannheim (DE); Volker Boehm, Frankenthal (DE); Andreas Brodhagen, Dannstadt-Schauernheim (DE); Frank Poplow, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 760 days.

(21) Appl. No.: 10/811,940

(22) Filed: Mar. 30, 2004

(65) Prior Publication Data

US 2004/0220441 A1 Nov. 4, 2004

(30) Foreign Application Priority Data

Apr. 30, 2003 (DE) .................................. 103 19 437

(51) Int. Cl.
*C07C 6/02* (2006.01)
(52) U.S. Cl. ..................................... 585/646; 585/643
(58) Field of Classification Search ................ 585/646; 17/643
See application file for complete search history.

(56) References Cited

U.S. PATENT DOCUMENTS

| | | | |
|---|---|---|---|
| 3,586,731 A | 6/1971 | Heckelsberg | |
| 4,024,201 A | 5/1977 | Takahashi | |
| 5,576,466 A | 11/1996 | Ledoux et al. | |
| 6,130,181 A | 10/2000 | Schwab et al. | |

FOREIGN PATENT DOCUMENTS

| | | |
|---|---|---|
| EP | 0 489 585 | 6/1992 |
| EP | 0 654 458 | 5/1995 |
| EP | 0 982 070 | 3/2000 |

OTHER PUBLICATIONS

J. C. Mol, Handbook of Heterogeneous Catalysis, vol. 5, chapt. 4.12.2, pp. 2387-2400, "Alkene Metathesis", 1997.
K. Weissermel, et al., Industrial Organic Chemistry, Fourth Edition, Chapt. 3.4, pp. 85-89, "Olefin Metathesis", 1994.
C. Pham-Huu, et al., Ind. Eng. Chem. Res., vol. 34, No. 4, pp. 1107-1113, "Reactions of n-Heptane and Methylcyclopentane Over an Oxygen-Modified Molybdenum Carbide Catalyst. Study of Coke Formation, Catalyst Deactivation, and Regeneration", 1995.
F. H. Ribeiro, et al., Journal of Catalysis, vol. 130, pp. 86-105, "Reactions of Neopentane, Methylcyclohexane, and 3,3-Dimethylpentane on Tungsten Carbides: The Effect of Surface Oxygen on Reaction Pathways", 1991.
El Mamoune Zahidi, et al., "Formation of Thermally Stable Alkylidene Layers on a Catalytically Active Surface", Letters to nature, vol. 409, XP-002299064, Feb. 22, 2001, pp. 1023-1026.
Jean-Yves Piquemal, et al., "Synthesis and Characterization of Highly Dispersed Molybdenum Carbides in Mesoporous Silica", Catalysis Letters, vol. 92 Nos. 3-4, XP-002299063, Feb. 2004, pp. 189-195.
S. T. Oyama, "Preparation and Catalytic Properties of Transition Metal Carbides and Nitrides", Catalysis Today, vol. 15, No. 2, XP-008032346, Jun. 30, 1992, pp. 179-200.
F. H. Ribeiro, et al., "Preparation and Surface Composition of Tungsten Carbide Powders with High Specific Surface Area", Chemistry of Materials, vol. 3, No. 5, XP-000247472, Sep. 1, 1991, pp. 805-812.

*Primary Examiner*—Thuan Dinh Dang
(74) *Attorney, Agent, or Firm*—Oblon, Spivak, McClelland, Maier & Neustadt, P.C.

(57) ABSTRACT

Process for preparing a compound having a nonaromatic C—C double or triple bond (compound A) from another compound or a mixture of other compounds having a nonaromatic C—C double or triple bond (compound B), which comprises bringing the compound (B) into contact with a heterogeneous catalyst comprising carbides or oxycarbides of a transition element at from 50 to 500° C.

20 Claims, No Drawings

PREPARATION OF OLEFINS BY METATHESIS OVER A CARBIDE OR OXYCARBIDE OF A TRANSITION METAL

The present invention relates to a process for preparing a compound having a nonaromatic C—C double or triple bond (compound A) from another compound or a mixture of other compounds having a nonaromatic C—C double or triple bond (compound B), which comprises bringing the compound (B) into contact with a heterogeneous catalyst comprising carbides or oxycarbides of a transition element at from 50 to 500° C.

In the present text, the term "heterogeneous catalyst comprising carbides or oxycarbides of a transition element" also encompasses a catalyst in which various transition elements are present side-by-side. Oxides and carbides can likewise be present side-by-side in the heterogeneous catalyst.

The metathesis of unsaturated compounds is a generally established method of breaking and rearranging C—C bonds (e.g. Mol, J. C., Chapt. 4.12.2 "Alkene Metathesis" in "Handbook of Heterogeneous Catalysis", Eds. Ertl, G., Knözinger, H., Weitkamp, J., VCH, Weinheim 1997; Weissermehl, K., Arpe, H.-J., Chapt. 3.4 "Olefin-Metathese" in "Industrielle Organische Chemie", 4th edition, VCH, Weinheim 1994). Numerous homogeneous catalysts have been developed, but separation of the catalyst from the reaction mixture is a particular problem here. Various types of catalysts have been described for heterogeneously catalyzed metathesis, too. For the temperature range up to 120° C., the use of supported $Re_2O_7$ or $Re(CO)_{10}$ catalysts is customary (Mol, J. C., Chapt. 4.12.2 "Alkene Metathesis" in "Handbook of Heterogeneous Catalysis", Eds. Ertl, G., Knözinger, H., Weitkamp, J., VCH, Weinheim 1997). However, rhenium is a rare and relatively expensive element, so that the use of such a catalyst is often uneconomical. At somewhat higher temperatures up to 400° C., catalysts based on $MoO_3$, $CoO$—$MoO_3$, $MoS_2$, $Mo(CO)_6$ or various supported Mo complexes can be employed according to the literature, and at even higher temperatures up to 540° C., systems based on $WO_3$, $WS_2$, $W(CO)_6$ or supported W complexes can be employed (Mol, J. C., Chapt. 4.12.2 "Alkene Metathesis" in "Handbook of Heterogeneous Catalysis", Eds. Ertl, G., Knözinger, H., Weitkamp, J., VCH, Weinheim 1997; Weissermehl, K., Arpe, H.-J., Chapt. 3.4 "Olefin-Metathese" in "Industrielle Organische Chemie", 4th edition., VCH, Weinheim 1994; Heckelsberg, L. F., Banks, R. L., Bailey, G. C., Ind. Eng. Chem. Prod. Res. Develop. 8 (1969), 259-261).

Although these are very inexpensive, they generally have a significantly lower activity and also display lower selectivities. The reduced selectivities are a consequence of double bond isomerization which proceeds in parallel to metathesis over the strongly acidic molybdenum and tungsten compounds at relatively high reaction temperatures, which leads to the formation of undesirable products.

To suppress the secondary reaction of double bond isomerization, U.S. Pat. No. 3,586,731 describes the addition of alkali metal salts or alkaline earth metal salts to silica-supported oxides, sulfides or hexacarbonyls of tungsten, molybdenum or rhenium. However, this can lead to a considerable decrease in the catalyst activity. U.S. Pat. No. 4,024,201 proposes adding halogen-containing compounds or amines to the feed to a supported $WO_3$ catalyst. However, such polar compounds are at the same time known as catalyst poisons in metathesis, so that a greatly reduced activity may also be expected here.

Carbides of transition metals have already been described as active catalysts for skeletal isomerization of hydrocarbons (Pham-Huu, C. et al., Ind. Eng. Chem. Res. 34 (1995), 1107; Ribeiro, F. H. et al., J. Catal. 130 (1991), 86). They are prepared, for example, by carbiding a catalyst precursor, for instance an $SiO_2$-supported Mo or W oxide, in a hydrocarbon-containing stream under reducing conditions at elevated temperatures. Various methods of preparing carbide catalysts are reported, for example, in Oyama, S. T., Catal. Today 15 (1992), 179.

It is an object of the present invention to provide a process for preparing unsaturated compounds, in particular olefins, by metathesis, in which the desired unsaturated compounds are formed at a high conversion and with high selectivity and the disadvantages of the above processes are at least partly avoided. In particular, the catalysts should display a high metathesis activity even at relatively low temperatures.

We have found that this object is achieved by the process defined at the outset.

Heterogeneous catalysts which comprise carbides or oxycarbides of a transition element and are suitable for the process of the present invention are generally known.

The catalyst preferably comprises molybdenum carbide, molybdenum oxycarbide, tungsten carbide, tungsten oxycarbide or a mixture of the abovementioned compounds.

The heterogeneous catalyst used is preferably a supported catalyst in which a carbide or oxycarbide of a transition element forms the active component (activator A) which has been applied to a customary support (support S). The proportion of activator (A) in the catalyst (C) is usually from 0.1 to 30% by weight.

Possible supports (support S) for the preparation of catalysts are all materials customarily used for the preparation of supported catalysts, for example metal oxides, nitrides, borides, carbides, silicates, activated carbon, graphite. Preference is given to compounds of main group elements or elements of transition group VI or II and also mixtures of the abovementioned compounds. Particular preference is given to $Al_2O_3$, aluminosilicates, $Ga_2O_3$, $SiO_2$, $GeO_2$, $TiO_2$, $ZrO_2$, $SnO_2$ and mixtures of the abovementioned compounds. Suitable supports typically have a specific surface area of 10-500 $m^2/g$, preferably 100-400 $m^2/g$. The preferred pore volume (determined by means of mercury porosimetry) is from 0.3 to 1.3 ml/g. The preferred water absorption is from 0.5 to 1.5 ml/g. The supports are usually shaped bodies such as spheres, granules, extrudates or pellets. The support may have additionally been pretreated with acids, bases or alcohols.

The preparation of the customary supported catalysts comprising carbides or oxycarbides as activator (A) is usually carried out by a.1) impregnating the support (S) with a solution of a compound of a transition element (step a.1), b.1) subsequently drying and then calcining the support (S) which has been impregnated in step a.1) (step b.1), c.1) heating the support (S) from step b.1 at from 550 to 1000° C. in an atmosphere comprising a hydrocarbon compound and hydrogen (step c.1)

In step (b.1), catalyst precursors having oxides as active components are formed. The preparation of such catalyst precursors is generally known. For example, the support S is impregnated in step (a.1) with a solution of compounds of the appropriate transition element. Such compounds are, for example, organic complexes, halides, acids, polyacids, heteropolyacids and salts of the acids, polyacids and heteropolyacids. Such salts are preferably alkali metal or ammonium salts. In the present context, organic complexes are, for example, dialkyl complexes, acyl compounds, acetylacetonates or allyl complexes. In the case of tungsten oxide, a solution of, for example, ammonium metatungstate, tungstic acid or tungsten pentachloride can be employed for this purpose. The impregnated supports are then usually dried in air at from 100 to 200° C. for a number of hours. This is usually followed by a calcination step. For this purpose, the impregnated and dried supports are usually-heated in an oxygen-containing gas atmosphere, e.g. in air, at from 400 to 850° C. for a period of from about half an hour to 5 hours. The catalyst precursors prepared in this way can also be pretreated by means of heating steps in inert gas, for example $N_2$, $CO_2$ or noble gases, or be partially reduced in reducing gas mixtures comprising, for example, hydrogen, CO, ammonia or hydrazine.

In the carbiding step (step c.1), the appropriate catalyst precursors comprising metal oxide are heated at from 550 to 800° C. in a hydrocarbon-containing stream, e.g. a methane stream, in the presence of hydrogen for, in general, a number of hours. The preparation of tungsten carbides typically requires temperatures about 50-200° C. higher than those for preparing molybdenum carbides. The properties of the carbides are also influenced by the $H_2/CH_4$ ratio which is typically 80/20. The appropriate carbiding methods are known and described, for example, in Oyama, S. T., Catal. Today, 15 (1992), 179.

After the carbiding step, these catalyst precursors have to be stored under an inert gas atmosphere because of their sensitivity to air, or they are passivated by means of dilute oxygen and then reactivated in the synthesis reactor. A further possibility is taking out the freshly prepared carbides under a liquid which substantially protects the carbide surface from atmospheric oxygen.

Furthermore, the following processes are also suitable for preparing catalyst precursors comprising carbides as activator precursors:

In J. Catal. 128, 126 (1991), Lee et al. describe the preparation of $Al_2O_3$-supported molybdenum carbides by (i) reduction followed by carbiding, (ii) direct carbiding in $CH_4/H_2$ or (iii) nitriding by means of $NH_3$ followed by carbiding.

Volpe, Boudart, J. Solid State Chem. 59, 332 (1985) and Volpe, Boudart, J. Solid State Chem. 59, 348 (1985) describe the nitriding/carbiding of $MoO_3$ and $WO_3$ in more detail.

The reduction of $MoO_3$ on carbon supports by means of hydrogen, which is coupled with carbiding by the carbon support at above 530° C., is described, for instance, in Liang et al., Chem. Mater. 2002, 14, 3148.

Oxycarbides which can be used as activator precursors are described, for example, in Pham-Huu et al., Appl. Catal. A 132 (1995), 77. They can be prepared from the oxides by only partial carbiding. The oxycarbides are also formed under suitable conditions during the reaction when the oxide is used as starting material and a hydrocarbon/$H_2$ mixture is then passed over the catalyst at elevated temperatures (for instance: $H_2$/n-hexane=150, T=350° C.

The oxycarbides can also be prepared by treatment of carbides with oxygen. In Ledoux et al., New Frontiers in Catalysis, 1993, p. 955, Guczi, L. et al (Editors), Elsevier Science Publishers B.V., the carbide is firstly treated with air at 350° C. and then with hydrogen at the same temperature.

Particularly good results are achieved using activated catalysts which are obtainable by a.2) applying a carbide or oxycarbide of a transition element to a customary support so as to produce a catalyst precursor (a.2) (step a.2), b.2) bringing the catalyst precursor (a.2) into contact with a hydrocarbon compound at from −20 to 550° C. (step b.2) and c.2) heating the catalyst precursor from step (b.2) at from 410 to 850° C. in an inert gas atmosphere (step c.2).

Step a.2) is generally carried out as described above for the customary heterogeneous catalysts comprising carbides or oxycarbides of a transition element, preferably as described in steps (a.1) to (c.1). The customary heterogeneous catalysts comprising carbides or oxycarbides of a transition element to be used according to the present invention thus serve in step (a.2) as catalyst precursors (a.2) for preparing the activated catalysts which are particularly preferably used in the process of the present invention.

In step (b.2), the catalyst precursors (a.2) are brought into contact with a hydrocarbon compound. Suitable hydrocarbon compounds are, in particular, aromatics, alkanes, cycloalkanes, alkynes, cycloalkynes, olefins or cycloolefins having from 1 to 20 carbon atoms. Particular preference is given to $C_3$-$C_{12}$-olefins, very particularly preferably butenes and octenes, e.g. 1-butene and n-1-octene.

In the treatment of the catalyst precursor with the hydrocarbon compound, the latter can be either in liquid or gaseous form. The treatment time is not critical and is usually 1 min-24 h, preferably 5 min-4 h. The temperature during the treatment is generally from −20 to 550° C., but is not critical. The latter also applies to the pressure, which is generally from 0.5 to 40 bar.

The catalyst precursor which has been pretreated with the hydrocarbon is subsequently heated to from 410 to 850° C., preferably from 500 to 850° C., in an inert gas atmosphere in step (c.2). Suitable inert gases are, in particular, nitrogen, $CO_2$ and the noble gases. The treatment in step c) is usually carried out for from 5 minutes to 100 hours, preferably from 30 minutes to 24 hours, with the pressure once again being noncritical and usually being from 0.5 to 40 bar.

The catalysts used may further comprise promoters. These are generally cobalt, alkali metal or alkaline earth metal compounds. They are generally applied to the catalyst by adding appropriate salts, e.g. nitrates or hydroxides, to the impregnation solutions used in step (a.1) for preparing the catalyst precursors, or by doping the catalysts afterward with an appropriate impregnation solution and calcining the catalysts once again to immobilize the dopant.

The process of the present invention is used to prepare a compound having a nonaromatic C—C double or triple bond (compound A) from another compound or a mixture of other compounds having a nonaromatic C—C double or triple bond (compound B). In the present text, the term compound (B) thus refers not only to a single compound but also to a mixture of various compounds, which leads to a cross-metathesis.

As compounds (B), use is advantageously made of appropriate hydrocarbons having from 2 to 12 carbon atoms. The compound (B) is preferably selected from the group consisting of $C_2$-$C_{12}$-olefins, substituted $C_2$-$C_{12}$-olefins and mixtures of the abovementioned compounds. In this context, substituted olefins are, for example, unsaturated acids, esters, nitriles, halides, ketones, aldehydes or amines.

The catalysts used according to the present invention can be employed particularly advantageously in metathesis processes for preparing propene by metathesis of a mixture comprising 2-butene and ethylene or 1-butene and 2-butenes, or for preparing 3-hexene and ethylene by metathesis of 1-butene. Appropriate processes are described in detail in DE-A-19813720, EP-A-1134271, WO 02/083609, DE-A-10143160.

The abovementioned $C_4$ starting compounds are usually supplied in the form of a raffinate II. The raffinate II is a $C_4$ fraction which generally has a butene content of from 30 to 100% by weight, preferbly from 40 to 98% by weight. Apart from butenes, saturated $C_4$-alkanes in particular can also be present. The way in which such raffinates II are obtained is generally know and is described, for example, in EP-A-1134271.

In particular, it is possible to use 1-butene which is obtained by distilling off a 1-butene-rich fraction from raffinate II. 1-Butene can likewise be obtained from the remaining 2-butene-rich fraction by subjecting the 2-butene-rich fraction to an isomerization reaction and subsequently fractionally distilling the product to give a 1-butene-rich fraction and a 2-butene-rich fraction. This process is described in DE-A-10311139.

The process of the present invention is generally carried out continuously in the gas phase. The temperature is generally from 100 to 500° C. The pressure is generally 5-50 bar.

The WHSV over the catalyst is generally from 1 to 30 g, preferably from 5 to 20 g, of compound (B) per g of catalyst per h.

EXPERIMENTAL PART

A. Preparation of the Catalysts Used

Preparation of a $WO_3/SiO_2$ Catalyst—Cat A 30 g of ammonium metatungstate (W content: 72.2%) were made up to 190 ml with $H_2O$. 200 g of an $SiO_2$ support (BASF D11-10, 1.5 mm extrudates, 171 m²/g) was impregnated with this solution. The extrudates were then dried at 120° C. for 16 hours in a drying oven. The catalyst was subsequently calcined at 593° C. in air (20 l/h) for 1 hour in a rotary tube furnace and cooled under dry nitrogen. The $WO_x$ content was 12.1 wt %.

XRD patterns of catalysts of this type removed from the reactor after the metathesis reaction described clearly showed substoichiometric $WO_x$ phases, predominantly $WO_{2.92}$. No carbidic species could be detected in this case.

Preparation of a Tungsten Carbide Catalyst—Cat B

To prepare catalyst B, 70 ml of the $WO_3/SiO_2$ catalyst A were placed in a glass reactor through which gas was passed from the top downward. The glass reactor was heated from the outside by means of an electric furnace, and the catalyst bed was located approximately in the middle of the heating zone on a glass frit. After the catalyst had been installed and the reactor had been closed, the plant was firstly flushed with nitrogen (30 min, 20 l/h). A gas stream comprising 3.9 l/h of methane and 15 l/h of hydrogen were subsequently passed over the catalyst. The reactor was then heated to 750° C. over a period of 180 minutes and held at 750° C. for 6 hours. It was then cooled to 500° C. over a period of 1 hour and this temperature was held for 2 hours. The reactor was then cooled and the methane/hydrogen stream was replaced by a stream of nitrogen. After the reactor had been flushed, the reactor inlet and outlet were closed and the reactor was removed from the plant in such a way that the catalyst could be transferred into a glove box without coming into contact with air. Contact with air was likewise avoided in subsequent handling of the catalyst, for instance the installation of the catalyst in the reactor or its introduction into analytical instruments.

An XRD (X-ray diffraction) pattern of the catalyst removed from the reactor after the metathesis reaction shows the compounds WC and $W_2C$ together with traces of metallic tungsten. $WO_x$ compounds are not observed.

Preparation of a Tungsten Carbide Catalyst—Cat C

To prepare catalyst C, 70 ml of the $WO_3/SiO_2$ catalyst A were placed in a glass reactor through which gas was passed from the top downward. The glass reactor was heated from the outside by means of an electric furnace, and the catalyst bed was located approximately in the middle of the heating zone on a glass frit. After the catalyst had been installed and the reactor had been closed, the plant was firstly flushed with nitrogen (30 min, 20 l/h). A gas stream comprising 3.9 l/h of propylene and 15 l/h of hydrogen were subsequently passed over the catalyst. The reactor was then heated to 400° C. over a period of 60 minutes, then to 650° C. over a period of 120 minutes and held at 650° C. for 5.5 hours. The reactor was then cooled and the propylene/hydrogen stream was replaced by a stream of nitrogen. After the reactor had been flushed, the reactor inlet and outlet were closed and the reactor was removed from the plant in such a way that the catalyst could be transferred into a glove box without coming into contact with air. Contact with air was likewise avoided in subsequent handling of the catalyst, for instance the installation of the catalyst in the reactor or its introduction into analytical instruments.

An XRD (X-ray diffraction) pattern of the catalyst removed from the reactor after the metathesis reaction tends to show an amorphous structure. $W_2C$ can be identified, and a species which might be $W_2N$ is also present. $WO_x$ compounds are not observed.

B. Metathesis Processes

Metathesis of 1-Butene Over Activated Catalysts A, B and C

About 35 g of catalyst A, B or C were in each case placed in an electrically heated tube reactor. A temperature of 190° C. was set at the entrance to the catalyst bed. A nonuniform temperature distribution of the heating led to a temperature rise through to the end of the catalyst bed (maximum temperature is in each case reported in brackets). As feed, pure 1-butene was fed in. The reaction pressure was 9.7 bar. Analysis of the output from the reactor was carried out on-line using a GC. Before the actual measurement, all catalysts had been activated by means of the following procedure: 1-butene is fed in under reaction conditions for 3-4 h and the catalyst is subsequently maintained at an internal temperature of 500° C. under flowing nitrogen (30 l/h) for 17 hours. The experimental results are shown in table 1.

TABLE 1

| Cat | T [° C.] | WHSV $h^{-1}$ | 1-Butene conversion [%] | Isomerization[1] [%] | Hexenes [mol %] | Propene [mol %] | $C_6$ selectivity [mol %] |
|---|---|---|---|---|---|---|---|
| A (comp.) | 189 (274) | 8.0 | 63.0 | 32.7 | 11.5 | 16.1 | 36.4 |
| B | 155 (238) | 4.3 | 44.1 | 13.9 | 13.5 | 6.9 | 61.1 |

TABLE 1-continued

| Cat | T [° C.] | WHSV h⁻¹ | 1-Butene conversion [%] | Isomerization[1] [%] | Hexenes [mol %] | Propene [mol %] | $C_6$ selectivity [mol %] |
|---|---|---|---|---|---|---|---|
| B | 190 (293) | 8.8 | 52.8 | 22.5 | 13.4 | 10.2 | 50.8 |
| C | 190 (240) | 8.8 | 48.9 | 22.2 | 11.4 | 9.1 | 46.7 |

[1]sum of the allyl fragments formed = [propene]/2 + 2-butenes + pentenes

Metathesis of 1-Butene Using Unactivated Catalysts A, B and C

The reaction was carried out as described above, but the activation procedure described there was omitted and the catalysts were supplied with 1-butene at the reaction temperature directly after installation. The experimental results are shown in table 2.

TABLE 2

| Cat | T [° C.] | WHSV [h⁻¹] | Rate (hexene) [mol/I$_{cat}$ * h] | Rate (propene) [mol/I$_{cat}$ * h] |
|---|---|---|---|---|
| B | 190 (303) | 8.8 | 0.16 | 0.70 |
| C | 190 (250) | 8.8 | 0.56 | 0.37 |
| C | 190 (253) | 13.2 | 0.30 | 0.75 |

When the experiment was repeated using a comparative catalyst which had been prepared as described in example 1 and had a WO₃ content of 13.9 wt % (WHSV=7.9; T=190 (256° C.)), no hexene or propene was detected.

We claim:

1. A process for preparing a compound having a nonaromatic C—C double or triple bond (compound A) from another compound or a mixture of other compounds having a nonaromatic C—C double or triple bond (compound B), which comprises bringing the compound (B) into contact with a heterogeneous catalyst comprising carbides or oxycarbides of a transition element at from 50 to 500° C. to convert compound B to compound A by metathesis.

2. A process as claimed in claim 1, wherein the compound (B) is selected from the group consisting of C2-C12-olefins, substituted C2-C12-olefins and mixtures of the abovementioned compounds.

3. A process as claimed in claim 1, wherein the heterogeneous catalyst is selected from the group consisting of molybdenum carbide, molybdenum oxycarbide, tungsten carbide, tungsten oxycarbide and mixtures of the abovementioned compounds.

4. A process as claimed in claim 1, wherein the heterogeneous catalyst is a supported catalyst in which a carbide or oxycarbide of a transition element forms an active component (activator A) which has been applied to a support (support S).

5. A process as claimed in claim 4, wherein the proportion of activator (A) in the supported catalyst is from 0.1 to 30% by weight.

6. A process as claimed in claim 4, wherein the heterogeneous catalyst is a supported catalyst whose support (S) is selected from the group consisting of Al2O3, aluminosilicates, Ga2O3, SiO2, GeO2, TiO2, ZrO2, SnO2 and mixtures of the abovementioned compounds.

7. A process as claimed in claim 4, wherein the supported catalyst is prepared by
   a.1) impregnating the support (S) with a solution of a compound of a transition element (step a.1),
   b.1) subsequently drying and then calcining the support (S) which has been impregnated in step a.1) (step b.1),
   c.1) heating the support (S) from step b.1 at from 550 to 1 000° C. in an atmosphere comprising a hydrocarbon compound and hydrogen (step c.1).

8. A process as claimed in claim 4, wherein the supported catalyst is prepared by
   a.2) applying a carbide or oxycarbide of a transition element to a support so as to produce a catalyst precursor (a.2) (step a.2),
   b.2) bringing the catalyst precursor (a.2) into contact with a hydrocarbon compound at from −20 to 550° C. (step b.2) and
   c.2) heating the catalyst precursor from step (b.2) at from 410 to 850° C. in an inert gas atmosphere (step c.2).

9. A process as claimed in claim 8, wherein said hydrocarbon compound is selected from the group consisting of $C_1$-$C_{20}$-alkanes, -cycloalkanes, -olefins, -cycloolefins, -alkynes, -cycloalkynes, aromatics and mixtures of the abovementioned compounds.

10. A process as claimed in any of claim 8, wherein said inert gas is selected from the group consisting of nitrogen, carbon dioxide and noble gases and mixtures thereof.

11. A process as claimed in claim 1, wherein said compound (B) is selected from the group consisting of hydrocarbons having from 2 to 12 carbon atoms, and mixtures thereof.

12. A process as claimed in claim 1, wherein said process is a process for preparing propene by metathesis of a mixture comprising 2-butene and ethylene or 1-butene and 2-butenes.

13. A process as claimed in claim 1, wherein said process is a process for preparing 3-hexane and ethylene by metathesis of 1-butene.

14. A process as claimed in claim 1, wherein said process is carried out continuously in the gas phase at a temperature from 100 to 500° C. and a pressure of 5-50 bar.

15. A process as claimed in claim 14, wherein the WHSV over the catalyst is 1 to 30 g of compound (B) per g of catalyst per h.

16. A process as claimed in claim 1, wherein said compound (B) is a raffinate II.

17. A process as claimed in claim 16, wherein said raffinate II has a butene content of from 30 to 100% by weight.

18. A process as claimed in claim 16, wherein said raffinate II has a butene content of from 40 to 98% by weight.

19. A process as claimed in claim 16, wherein said process is carried out continuously in the gas phase at a temperature from 100 to 500° C. and a pressure of 5-50 bar.

20. A process as claimed in claim 19, wherein the WHSV over the catalyst is 1 to 30 g of compound (B) per g of catalyst per h.

* * * * *